(12) United States Patent
Lesniak et al.

(10) Patent No.: US 8,978,999 B2
(45) Date of Patent: Mar. 17, 2015

(54) CONTAINER FOR AIR FRESHENING MATERIALS AND OTHER VOLATILES

(75) Inventors: Frank M. Lesniak, Media, PA (US);
Kyle Brandenburg, Middletown, DE (US); John R. Hickman, North Canton, OH (US)

(73) Assignee: Hayloft Enterprises, Inc., Wilmington, DE (US)

( * ) Notice: Subject to any disclaimer, the term of this patent is extended or adjusted under 35 U.S.C. 154(b) by 927 days.

(21) Appl. No.: 13/090,542

(22) Filed: Apr. 20, 2011

(65) Prior Publication Data
US 2012/0267279 A1    Oct. 25, 2012

(51) Int. Cl.
| | |
|---|---|
| A61L 9/12 | (2006.01) |
| A61L 9/04 | (2006.01) |
| B65D 51/16 | (2006.01) |
| B65D 43/24 | (2006.01) |
| B65D 41/04 | (2006.01) |

(52) U.S. Cl.
CPC ........................................ *A61L 9/12* (2013.01)
USPC ............................................. 239/57; 239/34

(58) Field of Classification Search
CPC .............. A61L 9/04; A61L 9/048; A61L 9/12; A61L 9/125; A01M 1/2055; B65D 43/18; B65D 43/24; B65D 51/16; B65D 51/1605; B65D 51/1622; B65D 51/1688; B65D 51/1672
USPC ............. 239/34, 53–59; 220/290, 212, 212.5; 215/238
See application file for complete search history.

(56) References Cited

U.S. PATENT DOCUMENTS

| | | | |
|---|---|---|---|
| 3,239,145 A | 3/1966 | Russo | |
| 3,908,906 A | 9/1975 | Crowle et al. | |
| 4,014,501 A * | 3/1977 | Buckenmayer | 239/58 |
| 4,372,490 A * | 2/1983 | Le Caire et al. | 239/59 |
| D306,478 S | 3/1990 | von Philipp et al. | |
| 5,180,107 A * | 1/1993 | Lindauer | 239/35 |
| D355,962 S | 2/1995 | Chiu et al. | |
| D368,771 S | 4/1996 | Patel et al. | |
| D392,032 S | 3/1998 | Zaragoza et al. | |
| D449,877 S | 10/2001 | Delmenico et al. | |
| D454,190 S | 3/2002 | Trocola | |
| D535,376 S | 1/2007 | Michaels et al. | |
| D544,084 S | 6/2007 | Michaels et al. | |

(Continued)

*Primary Examiner* — Darren W Gorman
(74) *Attorney, Agent, or Firm* — Panitch Schwarze Belisario & Nadel LLP

(57) ABSTRACT

A container for air freshening materials or other volatiles includes a receptacle or base and a cover that may be rotated from a closed position to multiple open positions while still engaged to the base to create vent passageway(s) between the cover and the base. A containment section of the base houses an air freshening material, such as a fragrance gel or potpourri, or a volatile, such as an insect repellant. The base further defines an alignment section adapted to rotationally and axially position the cover, an integrated sealing element, and an optional vent section. The alignment section includes a ramp and upper and lower locating elements coupled to the ramp. The alignment section engages at least one guide or a guide nub that extends from a depending arm of the cover. The guide or guide nub travels along the ramp from a first locating element when the cover is in a fully closed position to a second locating element when the cover is in a fully open position. In one of its multiple open positions, the cover is rotationally and axially displaced to specified height(s) above the container, allowing for fragrance or volatile material release.

10 Claims, 8 Drawing Sheets

(56) References Cited

U.S. PATENT DOCUMENTS

| | | |
|---|---|---|
| D544,593 S | 6/2007 | Yamamoto |
| D547,850 S | 7/2007 | Michaels et al. |
| D548,317 S | 8/2007 | Newton et al. |
| D562,144 S | 2/2008 | Lane |
| D583,451 S | 12/2008 | Aloe et al. |
| D583,452 S | 12/2008 | Aloe et al. |
| D598,770 S | 8/2009 | Delfino, Jr. |
| D614,277 S | 4/2010 | Hsiao |
| D628,281 S | 11/2010 | Bates et al. |
| D631,534 S | 1/2011 | Kajizuka |
| D635,403 S | 4/2011 | Conway et al. |
| D635,653 S | 4/2011 | Conway et al. |
| 8,251,299 B1 * | 8/2012 | Irvin ............... 239/58 |
| 8,485,454 B1 * | 7/2013 | Irvin et al. ........ 239/58 |
| 2011/0011947 A1 | 1/2011 | Wallis et al. |

* cited by examiner

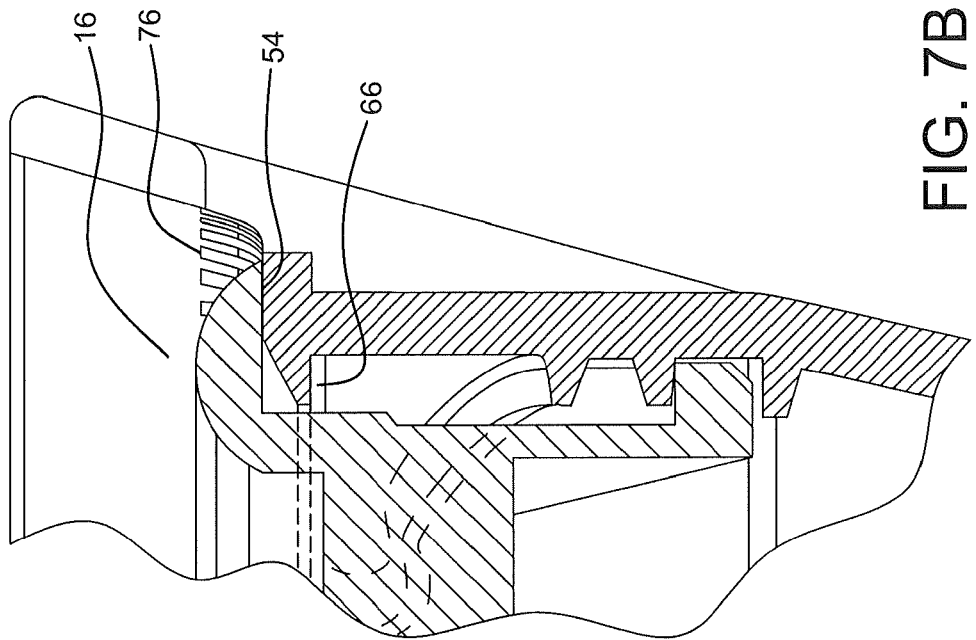
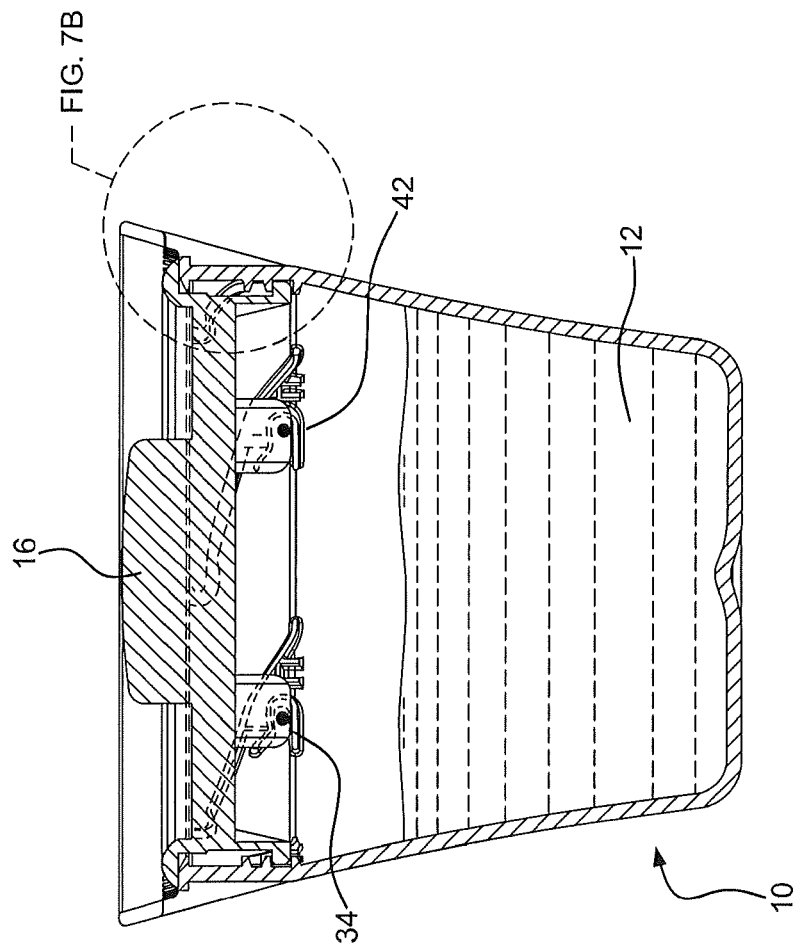
FIG. 7B
FIG. 7A

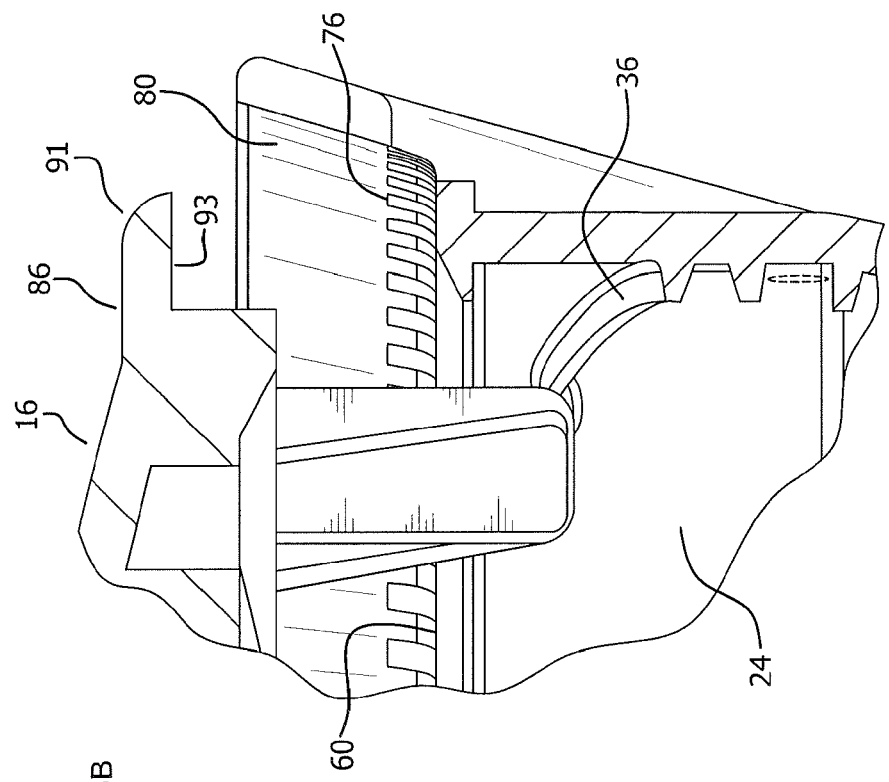
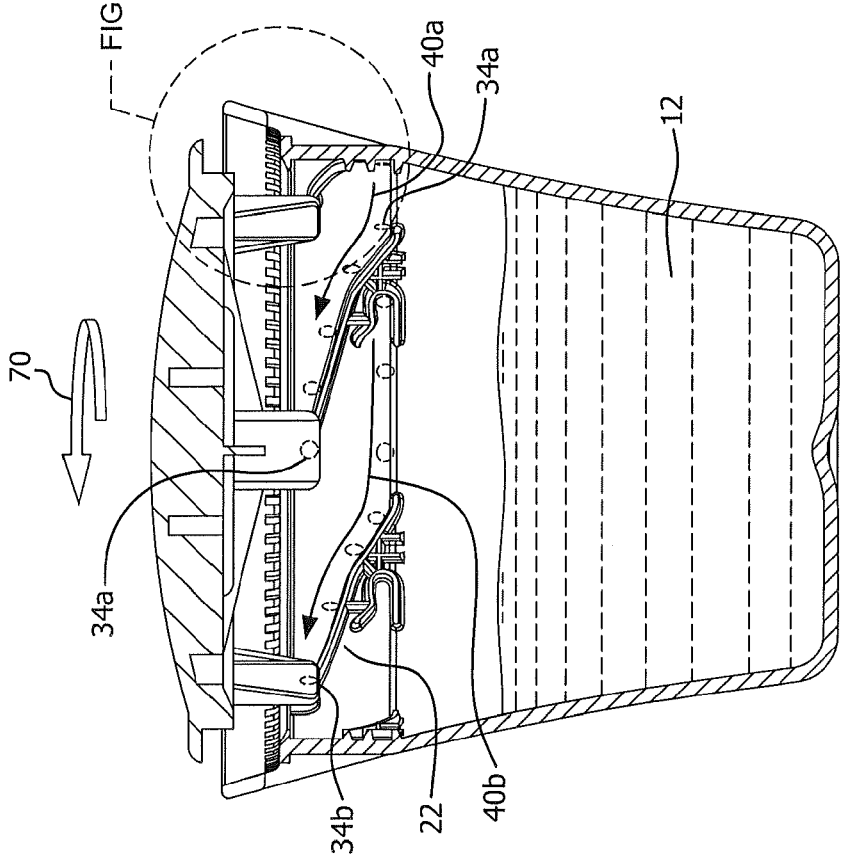

CONTAINER FOR AIR FRESHENING MATERIALS AND OTHER VOLATILES

BACKGROUND OF THE INVENTION

1. Field of the Invention

The field of the present invention is containers for air freshening materials and other volatiles or actives, particularly containers having a cover over a receptacle portion, wherein the cover is coupled to the receptacle portion for axial and rotational positioning.

2. Background

Containers for air freshening materials are sold in a variety of forms, depending, in part, on the type of fragrance material they are adapted to house and their expected placement in a home or business. Air freshening materials, such as gels, sachets, powders, and polymer beads, for example, are often housed in containers suitable for upright positioning on horizontal surfaces in a home, office or public space.

Many of these types of air freshening materials are sold in containers having a cover and a receptacle portion with a base. A cover may be coupled to the receptacle portion in a variety of ways. In some configurations, a cover is adhesively sealed onto the upper rim of the container. When fragrance release is desired, a user simply peels away and thereafter discards the cover. Fragrance release then continues until the air freshening material is dissipated or the fragrance power of the air freshening material diminishes. With this type of cover, the container does not provide a way to limit fragrance release after opening.

Alternatively, a cover and a receptacle portion may be coupled using threaded elements. Covers used with these types of containers, however, are separate components, and the cover is completely removed from the receptacle portion. Often these containers have an initial sealing element that breaks upon opening when the cover is twisted. To limit fragrance release after opening, a user must replace the cover. Once replaced, however, this type of cover may not sufficiently seal the container.

Other air freshener containers, such as those primarily used for gels, typically have a cover that is coupled to a receptacle portion, as well as a component that connects the receptacle portion and cover. These types of containers have gel positioned between the receptacle portion base and the cover such that the connecting component is surrounded by gel. To release fragrance, a user grips the cover and pulls it away from the base to expose the gel. These types of containers often allow for only axial displacement of a cover and also have only an initial seal that breaks upon opening. Containers of this type include the Renuzit Adjustable® Air Freshener manufactured by Dial.

Although useful for their intended purpose, the types of containers described have several limitations, particularly relating to their ability to control fragrance release after opening. Considering these limitations, among others, a clear need exists for improved containers for air freshening materials.

SUMMARY OF THE INVENTION

A container for one or more air freshening materials or other volatiles has a cover and receptacle or base. The cover is adapted for axial and rotational positioning with respect to the receptacle or base, and vent passageways are established between the cover and the receptacle and base while the cover remains engaged to the receptacle or base.

The receptacle or base preferably includes a containment section adapted to house an air freshening material, such as but not limited to a fragrance gel, or other volatile, an alignment section adapted to rotationally and axially position the cover with respect to the receptacle or base, an integrated sealing element, and one or more vent sections. The alignment section preferably is disposed on an inner wall of the receptacle or base. The alignment section further is adapted to engage with at least one guide that extends from a portion of the cover. Preferably, the cover is provided with a plurality of guide nubs extending from depending arms, and the base is provided with a corresponding plurality of alignment sections.

In one embodiment, the alignment section includes a ramp that directs the travel of the guide in contact therewith as the cover is rotated from a closed position to an open position. In addition, the alignment section may include upper and lower locating elements coupled to the ramp. These locating elements seat and releasably snap fit or lock guide nubs in place at varying positions. In a closed position, the cover is sealing engaged with the receptacle or base to limit the air freshening material or volatile from exposure to air. In an open position, the cover is rotationally and axially displaced to one or more specified heights above the container, creating vent passageways between the cover and the receptacle or base allowing for air exposure and fragrance or volatile release.

In the embodiments with guide nubs, each guide nub preferably is coupled to a downwardly extending arm disposed on the cover. The arms of the cover are coupled to a cover positioning element that further facilitates rotational and axial positioning of the cover.

The container also preferably includes a vent section having series of slots disposed in an array around an upper section of the receptacle or base.

BRIEF DESCRIPTION OF THE DRAWINGS

Numerous other features and advantages of the invention shall become apparent upon reading the following detailed description taken in conjunction with the accompanying drawings, in which:

FIG. 7A is a cross-sectional view of the container shown in FIG. 4 taken along line 5-5, but with the cover in a closed position;

FIG. 7B is an partial detail view of area 7B, as designated in FIG. 7A, showing the contact between a portion of the cover and an alignment section;

FIG. 8A is a cross sectional view of a container shown in FIG. 4 taken along line 5-5, and with the cover in an open position;

FIG. 8B is an partial detail view of an area 8B, as designated in FIG. 8A, showing the contact between a portion of the cover and an alignment section;

DETAILED DESCRIPTION OF THE PREFERRED EMBODIMENTS

Figure 1:
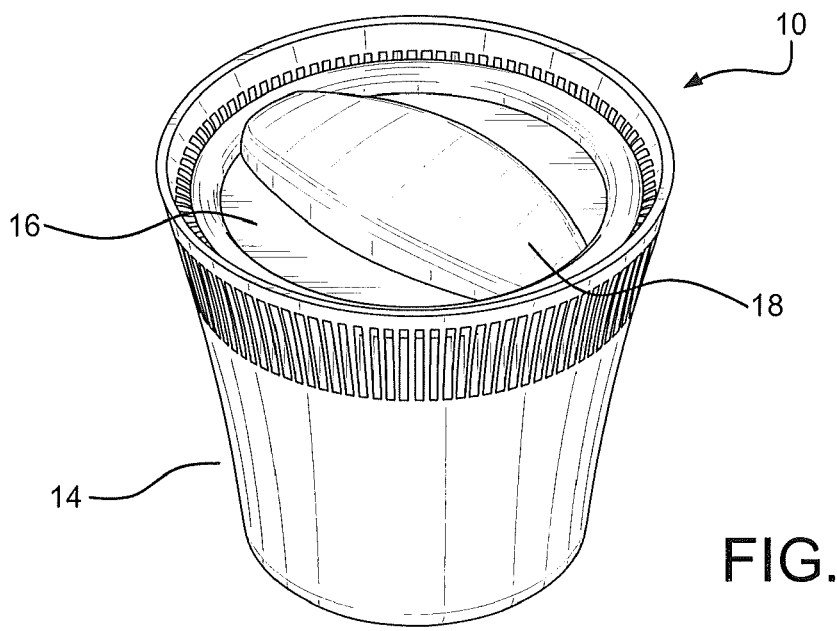
FIG. 1 is a perspective view of a container for air freshening materials or volatiles where the cover is in a closed position.

Turning in detail to the drawings, FIGS. 1-4 show a container 10 for an air freshening material or other volatile 12 (not shown) having a receptacle portion or base 14 and a cover 16. The cover 16 includes a gripping or positioning element 18 that facilitates rotation of the cover. As further described below, the cover 16 is coupled to the receptacle portion or base 14 for radial and axial displacement. Radial and axial displacement of the cover allow a user to control exposure of the air freshening material and fragrance or volatile release, as desired.

Preferably, the receptacle or base is molded from a thermoplastic material. These materials may contain one or more resins, such as polyvinylchloride (PVC), polyethylene (PE), polyethylene terephthalate (PET), polyoxymethylene (POM), polyamides (nylon), polypropylene, ethylene vinyl acetate, acrylonitrile butadiene styrene (ABS), and styrene-acrylonitrile, copolymers thereof, and mixtures thereof. Further, the resin composition is preferably mixed, blended, or compounded with additives to form an injection moldable material.

As shown particularly in FIGS. 5-8, the receptacle portion or base 14 includes a containment section 20 and one or more alignment sections 22. The containment section 20 includes a bottom surface 28 and containment inner wall(s) 30 and containment outer wall(s) 32. The containment inner wall(s) 30 and bottom surface 28 are adapted for chemical compatibility with an air freshening material 12 (shown in FIGS. 7A and 8A) or volatile held within the receptacle portion.

Air freshening materials, as used in herein, are broadly defined to include effluvia or other emanative materials, particularly materials that emanate fragrance. Such air freshening materials include, but are not limited to gels, potpourri, blot paper, oils, powders, polymer beads, sachets, and liquids. Representative air freshening gels include an aqueous composition comprising one or more gellants, fragrance oils, water, hydric solvents and optional cross-linking ions. Such gels have been known and are described in U.S. Pat. No. 2,927,055 (Lanzet), U.S. Pat. No. 3,969,280 (Sayce) and U.S. Pat. No. 4,056,612 (Lin), incorporated herein by reference. Alternatively or additionally, the air freshening materials may comprise or act as a volatile insecticide and/or insecticidal synergist or attractant or repellant, such as pyrethrum, octenol, linalool, mint oil, or a bacteriostat or pheromone. As still another alternative, the air freshening materials may comprise dessicant granules, particles, powders or materials. The air freshening material(s) or volatiles are poured or cast into the containment section of the receptacle portion.

Figure 5:
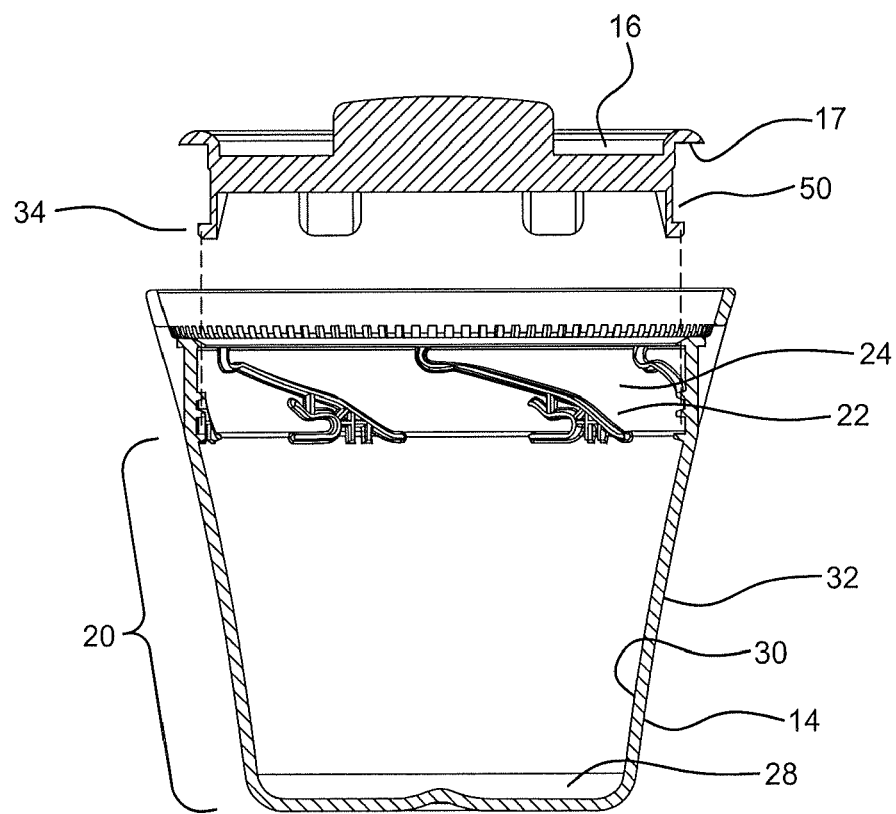
FIG. 5 is an exploded cross sectional view of the container shown in FIG. 4 taken along line 5-5 with the cover separated from the receptacle portion and shown positioned above the receptacle portion.

As shown particularly in FIG. 5, the cover 16 and receptacle portion or base 14 can be separate components adapted for alignment. To facilitate alignment, alignment sections 22 are adapted to engage with axially directed depending arms 50 disposed on the cover 16 or with guide nubs 34 extending radially from the axially depending arms 50 disposed on the cover 16. One or more alignment sections 22 are preferably disposed on the inner wall 24 of the receptacle portion or base 14. In one embodiment as illustrated in FIGS. 5-8, six alignment sections and six depending arms with radially extending guide nubs are provided. Fewer or more of these alignment elements may be provided, depending upon the size of the container 10, among other things.

Figure 6A:
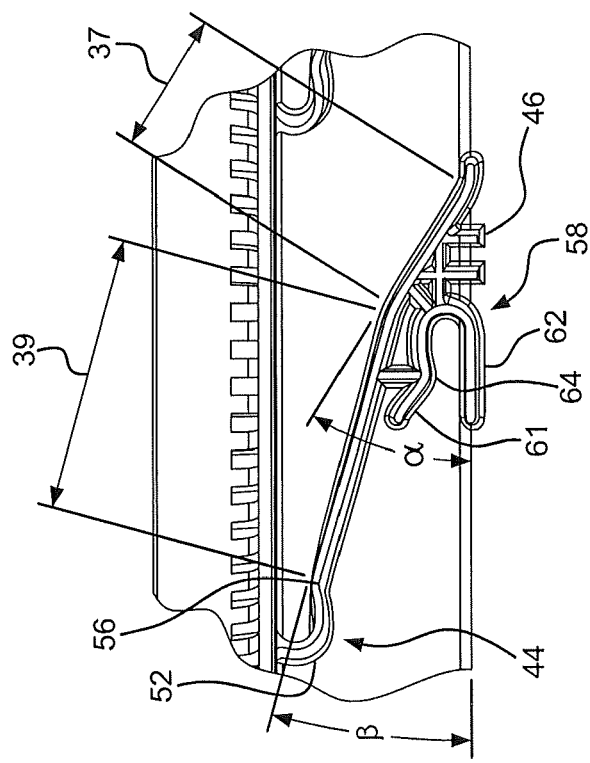
FIG. 6A is a partial detail view of the alignment section shown in FIG. 6.
Figure 6:
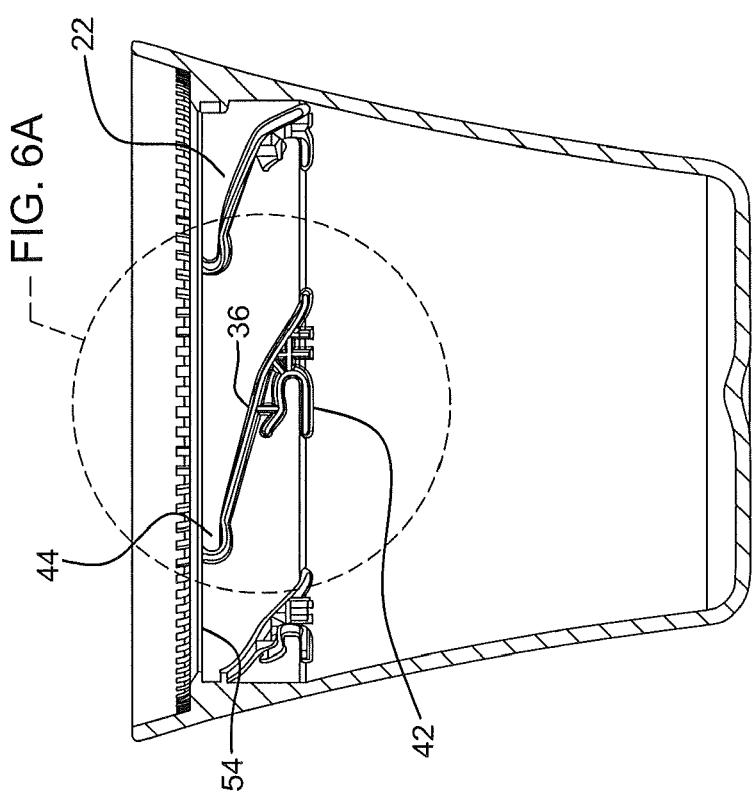
FIG. 6 is a cross-sectional view of the receptacle portion of the container shown in FIG. 3 taken along line 6-6.

As shown particularly in FIGS. 6 and 6A, each alignment section 22 includes a ramp 36 that allows for radial and axial displacement of the depending arms 50 (not shown in FIGS. 6, 6A) or guide nubs 34 (not shown in FIGS. 6, 6A). The ramp 36 extends radially inwardly into the container volume from the inner wall 24 such that each arm 50 or guide nub 34 extending from such arm 50 can travel on the ramp 36 along a path 40 (shown in FIG. 8A). Preferably, the ramp 36 is dimensioned with at least two sections disposed at different angles. In one configuration, the ramp 36 has a first section 37 disposed at an angle $\alpha$, ranging from 0 to about 60 degrees from horizontal and a second section 39 disposed at an angle $\beta$ ranging from 0 to about 40 degrees from horizontal, as shown particularly in FIG. 6A.

The alignment section 22 may also include a lower locating section 42 and an upper locating section 44. Each of these sections 42, 44 allows for guide nubs 34a, 34b to seat in specified areas. When the cover 16 is in a fully closed position, each guide nub 34a seats in a respective lower locating section 42. When the cover is in a fully open position, each guide nub 34b seats in a respective upper locating section 44. Preferably, the sections 42, 44 and the ramp 36 are integrally molded with the container 10.

Figure 9:
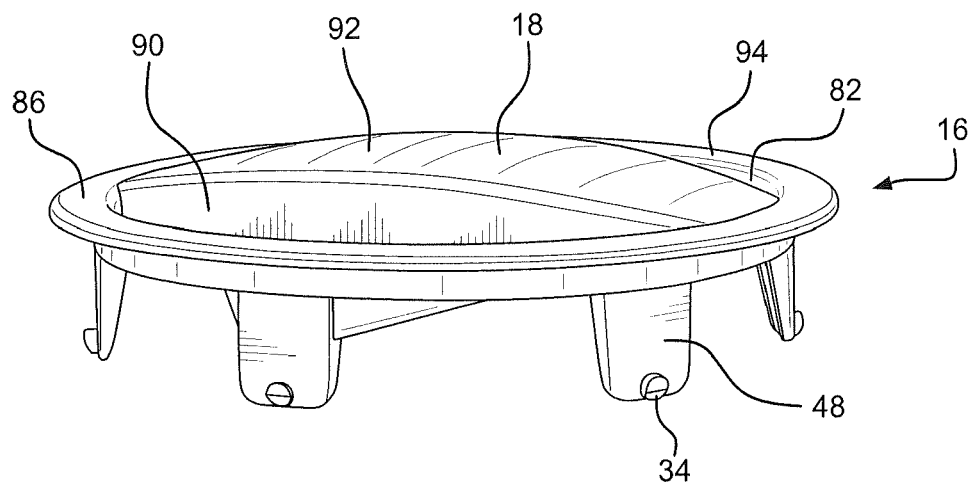
FIG. 9 is a top perspective view of the cover of FIG. 5.
Figure 10:
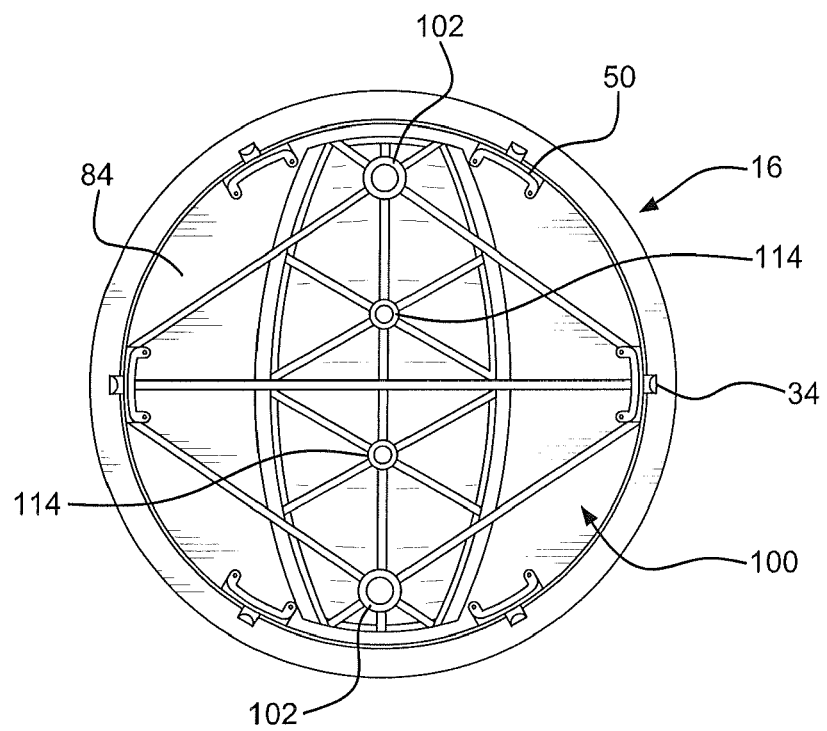
FIG. 10 is a bottom view of the cover of FIG. 5.

As shown in FIG. 6A, the lower and upper locating sections 42, 44 are curved to conform to the peripheral shape of guide nubs 34. In one configuration, the guide nubs 34 have a substantially circular cross-section, with tapered or slanted faces at their distal ends. As shown in FIG. 9, the guide nubs 34 have first and second slanted faces. The first or upper slanted face preferably slants at an angle complementary to the sidewall of the containment inner wall(s) 30 of the receptacle portion 14. The second or lower slanted face of each nub preferably slants at a slant angle different from the first or upper slanted face, and the second or lower slanted face contacts a respective ramp 36 of an alignment section 22. The guide nubs 34, however, may have any shape that facilitates travel along the ramp 36. The guide nubs 34 extend radially outwardly from an outer face 48 of the arms depending axially downwardly from the cover, as shown in FIGS. 9 and 10.

The upper locating section 44 has an upper curved section 52 into which a first guide nub 34 seats when the cover 16 is moved/rotated to its fully open position. The receptacle portion or base 14 is further adapted to have an annular rim 54 at which the upper locating section 44 terminates. Further, an upper interference area 56 may be provided where the ramp 36 and the upper locating section 44 interface. This area 56 is dimensioned such that the distance between the rim 54 and the upper interference area 56 releasably snap fits or locks the guide nub 34b in place with an interference fit with a reasonably amount of torque force applied to the cover gripping or positioning element 18. When the cover 16 is in a fully open position (FIGS. 2 and 3), the top portion of cover 16 is raised axially a distance above the upper rim of the receptacle portion 14 thereby defining vent passageways 15 (FIG. 2) between the cover 16 and the upper rim of the receptacle portion 14.

A user may position the cover 16 in an open position different from the fully open position by rotating the cover 16 such that the guide nubs 34 contact a portion of the alignment section 22, such as along first section 37 or along second section 39 (FIG. 6A), but without continuing to rotate the cover 16 so that the guide nubs 34 seat into the upper locating sections 44. With these varying open positions, the user may minimize or increase the size of the vent passageways 15, and in turn minimize or increase the amount of air that may enter the containment section and come in contact with the air freshening material or volatile held therein.

The lower locating section 42 has a lower curved section 58 into which a different guide nub 34 may seat when the cover 16 is in a lower or fully closed position. In addition, the lower locating section 42 has a path guide section 61 and a linear guide section 62 that further facilitate alignment and positioning of the different guide nub 34. The lower locating element may also be provided with a lower interference area 64. Preferably, this area 64 is provided where the path guide section 61 and the curved section 58 interface. The interference area 64 allows the guide nub 34 to releasably snap fit or lock in the lower position. The interference area 64 is similarly dimensioned such that a user may move/rotate the guide nub 34 upon application of reasonable torque.

Preferably, between the ramp 36 and the lower locating sections 44 are filling ribs 46. These filling ribs 46 reinforce the alignment section 22 and help to prevent incorrect placement of the guide nubs 34 therein.

As shown in FIGS. 7A and 7B, before opening, the container 10 is provided in a fully closed position. In this position, each guide nub 34 is seated in a respective lower locating section 42. When the container 10 is closed, the cover 16 is seated with the cover rim 17 substantially flush against the container annular rim 54, which seals the container and limits limits emission of fragrance or volatile from the air freshening material 12. To further limit exposure of the air freshening material 12, the container 10 optionally is provided with an additional sealing element 66. The sealing element 66 preferably is integrally molded with the receptacle portion or base 14 and forms a radially inwardly extending rim, which extends towards the inner volume of the container 10 and contacts a sidewall portion of the cover 16 when the cover is closed, further sealing the air freshening material 12 from exposure to air. Still other sealing elements (not shown), such as a gasket or liner or coating, may be installed between the cover rim 17 and the annular rim 54 of the container 10.

As shown in FIG. 8A, upon counter-clockwise rotation of the cover 16, as indicated by arrow 70, the cover 16 is rotationally and axially positioned to open the container 10. During this rotation, guide nubs 34a, 34b represented schematically in FIG. 8A, travel along paths 40a, 40b in a respective alignment section 22 to an upper position. In this upper position, the cover 16 is thereby rotationally and axially displaced to a specified height above the receptacle portion or base 14, establishing a gap or gaps or vent passageways 15 (FIG. 2) between the cover 16 and the base 14 through which air may enter and allowing for fragrance or volatile release into such air.

For assembly, once the air freshening material or volatile is dispensed into the containment section of the receptacle portion 14, the cover 16 may be snapped over the receptacle portion 14. In a particularly preferred embodiment, the guide nubs 34 extending from the depending guide arms 50 are tapered to help snap fit the cover into position. The tapered and slanted faces of the guide nubs 34 help to (a) sink the cover into the receptacle portion by permitting flexing of the arms 50, and (b) self-locate the cover 16 so that the nub portions are in contact with the respective ramp portions 36 of the alignment sections 22. This embodiment is particularly advantageous because the cover 16 may be installed over the receptacle portion 14 with the depending arms 50 in any rotational location without need for exact registering, and the depending arms will self-locate with guide nubs 34 onto a respective alignment section 22.

Figure 2:
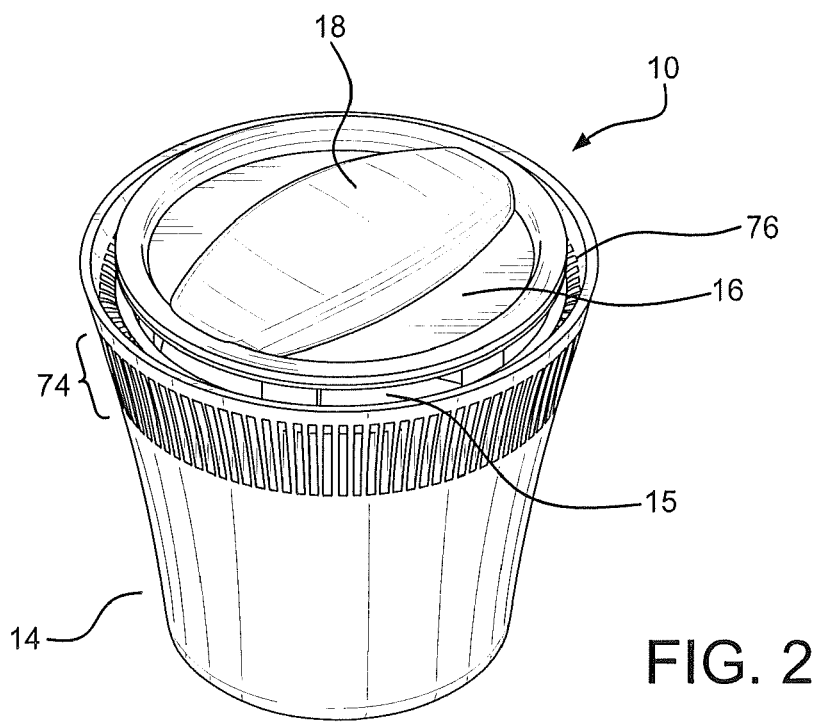
FIG. 2 is a perspective view of the container of FIG. 1 where the cover is in an open position.

As shown particularly in FIGS. 2 and 8B, the receptacle portion or base 14 optionally can further include a vent section 74 having vents 76 that extend at least in part above the rim 54. The vents 76 facilitate additional air flow into the internal volume of the base 14 and across the air freshening material 12. For additional seating of the cover 16, a vent wall 60 is provided. Optionally, for aesthetic purposes, vent ribbing 78 is incorporated in an upper section of the outer wall 80 of the base 14 (shown in FIGS. 1-3).

Figure 3:
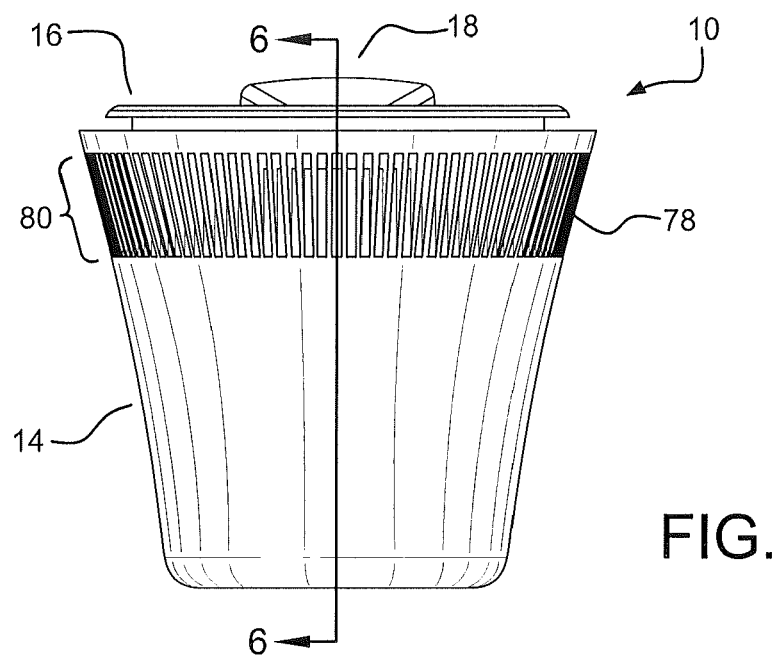
FIG. 3 is a side elevational view of the container shown in FIG. 2.
Figure 4:
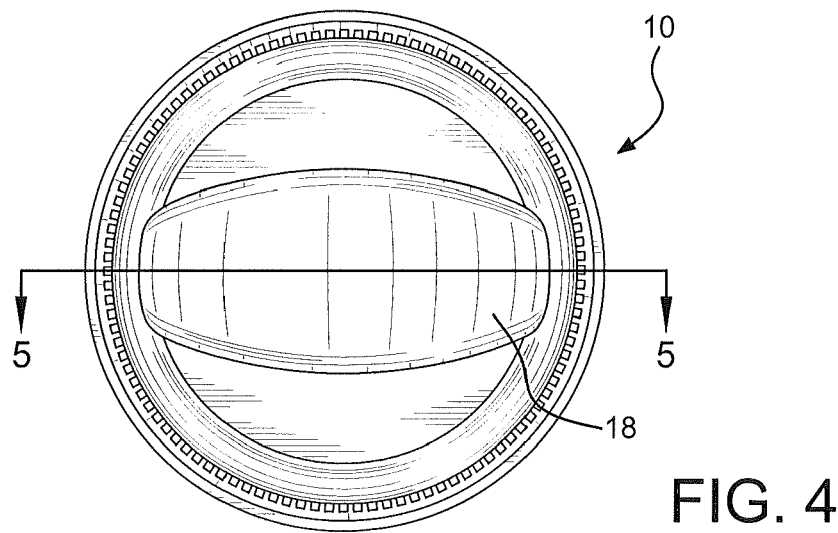
FIG. 4 is a top elevational view of the container shown in FIG. 2.

As shown in the embodiment of FIGS. 1-3, the optional vents 76 are parallel, vertically aligned, straight, generally rectangular, spaced-apart slots that are aligned in an array or arranged in a row about the circumference of the upper section of the outer wall 80 of the base 14. The vents 76 of this configuration also provide gripping means for grasping the container when moving the cover 16 from a closed position (FIG. 1) to an open position (FIG. 2). The upper ends of the slots extend through the thickness of the base outer wall, each defining a slot opening. The lower ends of the slots optionally have a depth that is less than the thickness of the base outer wall, such that the lower ends of the slots define a crevice or recess that retains a back wall.

Figure 11:
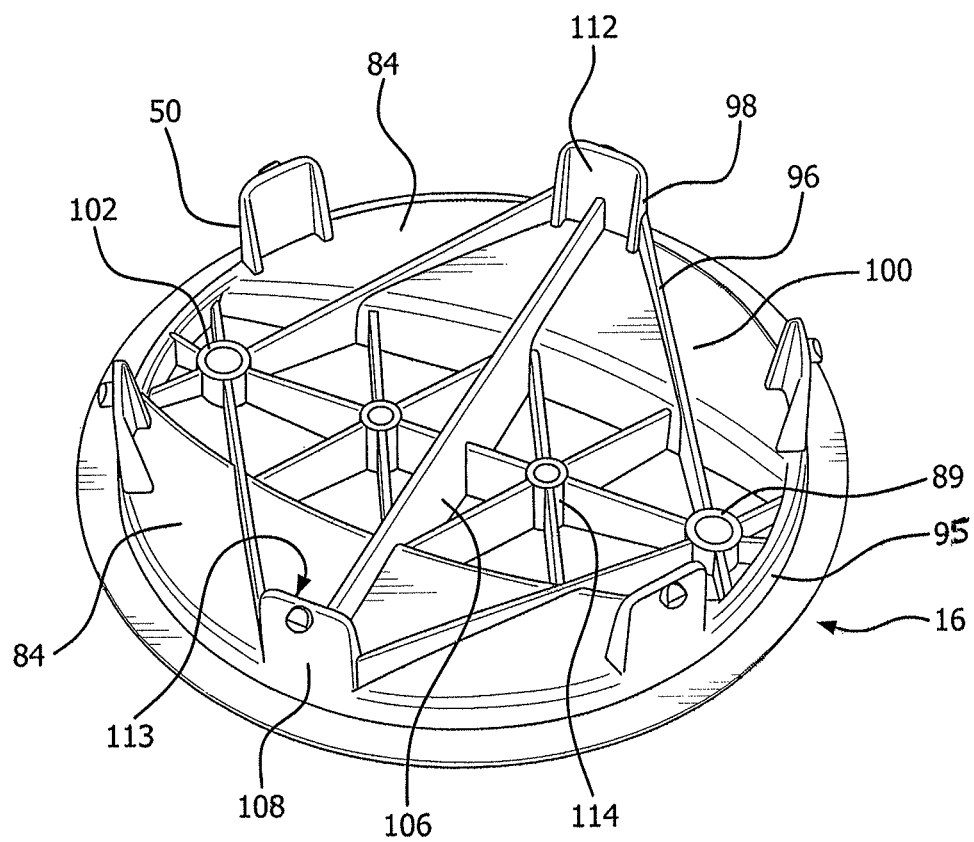
FIG. 11 is a bottom perspective view of the cover shown in FIG. 10.

As shown, particularly in FIGS. 9-11, the cover 16 includes elements that allow for positioning of the cover, as well as reinforcement or ribbing elements 100 that limit warping of the cover. In preferred embodiments, the cover 16 is removably engaged to the base 14, such that the cover 16 locates and aligns with one or more alignment sections 22.

Preferably, the cover 16 is injection molded from a thermoplastic material. The thermoplastic material may contain one or more resins such as polyvinylchloride (PVC), polyethylene (PE), polyethylene terephthalates (PET), polyoxymethylene (POM), polyamides (nylon), polypropylene, ethylene vinyl acetate, acrylonitrile butadiene styrene (ABS), and styrene-acrylonitrile, copolymers thereof, and mixtures thereof. Further, the resin composition is preferably mixed, blended, or compounded with additives to form an injection moldable material. Additionally, the material may include pigments used to differentiate the cover from the base. Such pigments include those manufactured by J. Meyers.

As shown in FIG. 9, the gripping or positioning element 18 is disposed between cover top walls 82 cover bottom walls 84 to prevent warping upon rotation of the gripping or positioning element 18. Cover top walls 82 are generally planar and lie below an annular mounting section 86. The gripping or positioning element 18 includes top sidewalls 90, positioning top wall 92 and top edges 94. Each top sidewall 90 transitions into each cover top wall 82. In addition, top edges 94 transition into the annular mounting section 86. The annular mounting section 86 preferably has a curved top profile 91 and a straight bottom profile 93, as shown in FIG. 8B. In addition, the positioning top wall 92 may include any type of identifying or advertising indicia, for example, product names and/or trademarks.

As shown in FIGS. 10 and 11, ribbing elements 100 preferably form a cross-ribbed structure having a symmetrical configuration. The cover includes cover bottom walls 84 with arms 50 coupled to cover outer wall 95. In this configuration, six arms 50 are spaced equidistantly around the outer wall 95. In addition to the guide nubs 34, side ribs 96 are coupled to at least two arms 50. These side ribs 96 extend from edges 98 to the ribbing bottom wall 89. Preferably, the side ribs 96 are positioned diagonally to terminate at outer nodes 102. Outer nodes 102 are also coupled to cover inner walls 104 for additional structural reinforcement.

Support rib 106 preferably is disposed between two supported arms 108. The support rib 106 extends from inner face 112, transitions to ribbing bottom wall 89, and further transitions to opposing inner face 113. The cross-ribbed structure preferably includes inner ribs 114 coupled to inner nodes 116. Preferably, an inner rib 114 extends from an inner node 116 to support rib 106, positioning inner walls 118, and to outer nodes 102. The aforementioned structure of ribbing elements 100 therefore reinforces the cover and prevents warping of the cover when the resin material is cooling and when the cover 16 is subjected to varied loading permutations and stresses.

While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A container for an air freshening material or volatile, comprising:
    a containment section adapted to house the air freshening material or volatile, said containment section having a sidewall with an inner surface and defining an inner volume;
    a first alignment section disposed on the inner surface of the sidewall of the containment section, said first alignment section having a first raised ramp integral with or coupled to the containment section and extending from the inner surface into the inner volume and adapted for guiding axial and rotational positioning of a container cover in relation to the containment section to create one or more vent passageways for air to flow into and out of the containment section, wherein the first alignment section further comprises at least one upper locating element adapted to seat at least one guide nub extending from the container cover when the container cover is in one open position when the at least one guide nub is in contact with a first end of the first raised ramp, and at least one lower locating element adapted to seat the at least one guide nub or another guide nub extending from the container cover when the container cover is in a closed position, said at least one lower locating element being at an opposite end of the first raised ramp; and
    a second alignment section disposed on the inner surface of the sidewall of the containment section in a position that is spaced apart circumferentially from the first alignment section, said second alignment section having a second raised ramp integral with or coupled to the containment section and extending from the inner surface into the inner volume and adapted for guiding axial and rotational positioning of the container cover in relation to the containment section, wherein the second alignment section further comprises at least one second upper locating element adapted to seat at least one other guide nub extending from the container cover when the container cover is in the open position when the at least one other guide nub is in contact with a first end of the second raised ramp, and at least one second lower locating element adapted to seat the at least one other guide nub or another guide nub extending from the container cover when the container cover is in a closed position, said at least one second lower locating element being at an opposite end of the second raised ramp.

2. The container of claim 1, further comprising a vent section adapted to facilitate air flow into and out of the containment section.

3. The container of claim 1, further comprising a container cover adapted to couple with the alignment section.

4. The container of claim 2, wherein the vent section comprises a plurality of vents formed through the sidewall of the containment section.

5. The container of claim 4, wherein the vents are slots arranged in a row about the circumference of an upper section of the sidewall.

6. The container of claim 1, wherein said first raised ramp has a first section disposed at a first angle from horizontal and has a second section disposed at a second angle from horizontal different from the first angle.

7. A container for an air freshening material or volatile, comprising:
    a containment section adapted to house the air freshening material or volatile, said containment section having a sidewall with an inner surface and defining an inner volume;
    a container cover adapted for rotational engagement with the containment section, said container cover having a plurality of guide nubs extending therefrom; and
    a plurality of raised alignment sections disposed on the inner surface of the sidewall of the containment section and extending from the inner wall into the inner volume, with each raised alignment section in a position that is spaced apart circumferentially from an adjacent raised alignment section, each raised alignment section adapted for contact with at least one of the plurality of guide nubs for guiding axial and rotational positioning of the container cover in relation to the containment section to create one or more vent passageways for air to flow into and out of the containment section, wherein each raised alignment section comprises at least one upper locating element adapted to seat one respective guide nub of the plurality of guide nubs and each raised alignment section comprises at least one lower locating element adapted to seat a different one of the guide nubs of the plurality of guide nubs,
    wherein irrespective of circumferential orientation when the container cover initially is inserted into the containment section for engagement therewith, said guide nubs orient or self-locate onto respective raised alignment sections.

8. The container of claim 7, wherein each guide nub extends radially from an arm depending axially from the container cover.

9. The container of claim 7, wherein each guide nub has a slanted face.

10. The container of claim 7, wherein the at least one upper locating element of one of the raised alignment sections is adapted to seat at least one of the plurality of guide nubs extending from the container cover at a first end of the one of the raised alignment sections when the container cover is in one open position, and the at least one lower locating element of the same raised alignment section is adapted to seat another of the guide nubs extending from the container cover at an opposite end of the one of the raised alignment sections when the container cover is in a closed position.

* * * * *